United States Patent [19]

Bicz

[11] Patent Number: 5,515,298
[45] Date of Patent: May 7, 1996

[54] APPARATUS FOR DETERMINING SURFACE STRUCTURES

[75] Inventor: Wieslaw Bicz, Wroclaw, Poland

[73] Assignee: Sonident Anstalt Liechtensteinischen Rechts, Vaduz, Liechtenstein

[21] Appl. No.: 220,712

[22] Filed: Mar. 30, 1994

[30] Foreign Application Priority Data

Mar. 30, 1993 [DE] Germany .......................... 43 10 390.1

[51] Int. Cl.⁶ .......................... G01N 24/00; G01N 29/00; G01N 29/18
[52] U.S. Cl. .......................... 364/556; 364/507; 364/506; 73/607; 73/620; 128/661.01; 128/661.02
[58] Field of Search .................. 73/602, 620, 625, 73/606, 607, 626; 364/506, 576, 556; 340/825.34; 382/4

[56] References Cited

U.S. PATENT DOCUMENTS

| | | | |
|---|---|---|---|
| 4,530,241 | 7/1985 | Crutzen et al. | 73/602 |
| 4,947,351 | 8/1990 | Moran et al. | 364/507 |
| 5,062,297 | 11/1991 | Hashimoto et al. | 73/602 |
| 5,117,692 | 6/1992 | Moser | 73/626 |
| 5,235,982 | 8/1993 | O'Donnell | 73/625 |
| 5,258,922 | 11/1993 | Grill | 364/506 |

Primary Examiner—Emanuel T. Voeltz
Assistant Examiner—Kamini S. Shah
Attorney, Agent, or Firm—Herbert Dubno

[57] ABSTRACT

For determination of surface and special surface characteristics of an object, e.g. a fingerprint, the finger tip is placed on a convex surface of a support which is irradiated through a liquid or solid medium with spherical ultrasonic waves from a point source provided as a hole in a carrier for a ring of receiving transducers.

20 Claims, 3 Drawing Sheets

APPARATUS FOR DETERMINGING SURFACE STRUCTURES

FIELD OF THE INVENTION

The present invention relates to an apparatus for determining surface structures and structures proximal to the surface of an object with ultrasonic waves. More particularly the invention relates to an apparatus for determining the structure of a fingerprint or the like.

BACKGROUND OF THE INVENTION

Apparatus for ultrasonic determination of surface structures and subsurface structures of an object is described in DE OS 40 16 105 A1 which corresponds in part to U.S. Pat. No. 5,258,922. This apparatus permits an object placed upon a planar or domed support which is transmissive to ultrasonic waves to be determined by transmitting the ultrasonic waves through a liquid or a solid body onto the object, and detecting the ultrasonic waves which are backscattered and reflected from that object.

From the intensity of the backscattered surface, characteristics of the surface of the object and subsurface or surface-adjacent structures can be determined. The transmitter of the ultrasonic waves and the receiver are disk-shaped and separate from one another. The transmitter in this system had to be designed to produce planar or spherical waves parallel to the surface and the receiver could only be one which was sensitive to such waves. In this manner the receiver effected directly a Fourier transformation from which respective parameters of the received waves, like phase amplitude or intensity, could be derived. Depending upon the structure of the object subjected to the ultrasonic waves, the scattering and hence the intensity of the back-scattered waves in the different direction can strongly differ. From the intensity values measured results like numerical values, color displacement or the like can be generated which reflects the surface pattern of the object for use in, for example, identification.

While this system has been found to be largely satisfactory, experience with it has shown that the results were highly dependent on the positioning of the object on the support.

OBJECTS OF THE INVENTION

It is, therefore, the principal object of the invention to provide an improved apparatus for the purposes described which is free from the mentioned drawback of the earlier system.

Another object of this invention is to improve upon the device described in the commonly-owned aforementioned patent so that the sensitivity of the results to the position of the object, e.g. a finger whose fingerprint pattern is to be determined, can be reduced or eliminated.

A more general object of this invention is to provide a more precise and reliable apparatus for determining surface and surface-adjacent structures of an object.

Still another object of the invention is to provide an ultrasonic imaging apparatus for determining or identifying surface and surface-adjacent structures which can effect a uniform irradiation of the object and a uniform reproduction of the surface of surface-adjacent structures independent of the position of the object.

SUMMARY OF THE INVENTION

These objects are attained, in accordance with the invention, in an apparatus for determining and/or identifying surface and subsurface structures of an object lying on a support, utilizing ultrasonic waves transmitted to the support through a liquid or a solid and by detecting backscattered ultrasonic waves from the object.

According to the invention, the detector is a receiver or converter (receiving transducer) arranged upon a support having a spherical concave surface turned toward the support upon which the object is provided and formed with a hole whose diameter is of the order of magnitude of the wavelength of the ultrasonic waves to ten times that wavelength. The transmitting transducer focuses its emitted ultrasonic waves at a focal point in the hole of the carrier so that the hole reemits the ultrasonic waves uniformly over the entire object as a point source of the ultrasonic waves of a spherical wavefront pattern. The center of curvature of the spherical surface lies at the center of the support which is also designed to focus the ultrasonic waves.

The hole functions as a pinhole and, because of its small diameter and its location at the focal point of a focusing emitting or transmitting transducer, enables a highly intensive and uniform irradiation of the entire object on the support. The hole is spaced sufficiently from the support surface on which the object is disposed that the latter, at least for the surface in contact with the support, is fully and completely irradiated by the ultrasonic surface. The plate irradiation of the object is an important characteristic of the apparatus of the invention. The point source character of the hole ensures that only spherical waves will reach the object.

It should be understood that waves emitted from an ultrasonic wave-generating transducer are normally not homogeneous and are not precisely spherical. The apparatus of the invention thus has a spectral purity and can ensure that only spherical waves reach the object. More particularly, the ultrasonic apparatus according to the invention can comprise:

a support transmissive to incident, reflected and backscattered ultrasonic waves formed with a resting surface upon which a surface to be determined of an object can rest;

receiving means comprising a body spaced from the support to a side thereof opposite the resting surface, having a spherically concave surface turned toward the support and having a center of curvature at a middle of the resting surface, and provided with a throughgoing hole having a diameter from an order of magnitude of a wavelength of the ultrasonic waves up to ten times the wavelength, the receiving means including transducer means responsive to ultrasonic backscattered waves from the object for outputting signals characterizing the surface to be determined, the support focussing ultrasonic waves toward the body;

an ultrasonic wave transmitting medium filling space between the receiving means and the support for transmitting ultrasonic waves emitted from the hole to the support and the object on the resting surface and the backscattered waves from the object to the receiving means and the transducer means; and a transmitting transducer disposed on an opposite side of the hole from the support for outputting ultrasonic waves and focussing the outputted ultrasonic waves upon the hole as a focal point for the outputted ultrasonic waves, whereby ultrasonic waves are emitted from the hole as a point source of spherical waves into the medium and onto the support for simultaneous irradiation of the entire surface of the surface of the object resting upon the surface with the spherical waves.

Preferably, the receiving transducer is disposed in a ring which can be constituted of a multiplicity of practically point-shaped transducers. A minimum number of preferably 256 such transducers can be assembled into the ring array, the diameter of the inlet window or aperture of each such transducer being of the order of magnitude of the wavelength of the ultrasonic radiation used.

So that sufficient energy will be directed to the receiving transducer ring, the support for the object can be formed as a concavo-convex or convexo-concave lens with the object preferably resting on a convex side thereof. Instead of a lens, the support surface can be provided by the convex side of a convexo-concave disk of uniform thickness. This ensures a focusing effect of the support in the direction of the receiving transducer ring. The waves which are not bent or scattered from the object are reflected back to the transmitter.

To determine the surface structure and surface-adjacent structures of the object, I prefer to use a group of pulses in a burst. It has been found that 3,000 pulse groups per second can be emitted and transmitted over a distance of about 10 cm between the hole and the support surface for the object. In order to obtain a complete diffraction image, it is necessary to operate with different frequencies in the ultrasonic range which are transmitted in succession. For each frequency, each receiving transducer is scanned individually. The scanning can be effected preferably with 20 different frequencies in the ultrasonic range. Under these conditions (see the aforementioned patent for details as to the electronics involved), the diffraction image is obtained with a satisfactory resolution. The frequency generator can apply pulse groups with the selected frequency via an amplifier to the transducer.

The waves backscattered from the object are recovered through an amplifier. The amplified signal is supplied to a detector which transforms the signal into a direct current. The average amplitude is then obtained over a predetermined time segment and after processing in the computer which also receives an input from the frequency generator, an appropriate output can be obtained. The details of the circuit can be derived from the aforementioned U.S. patent.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
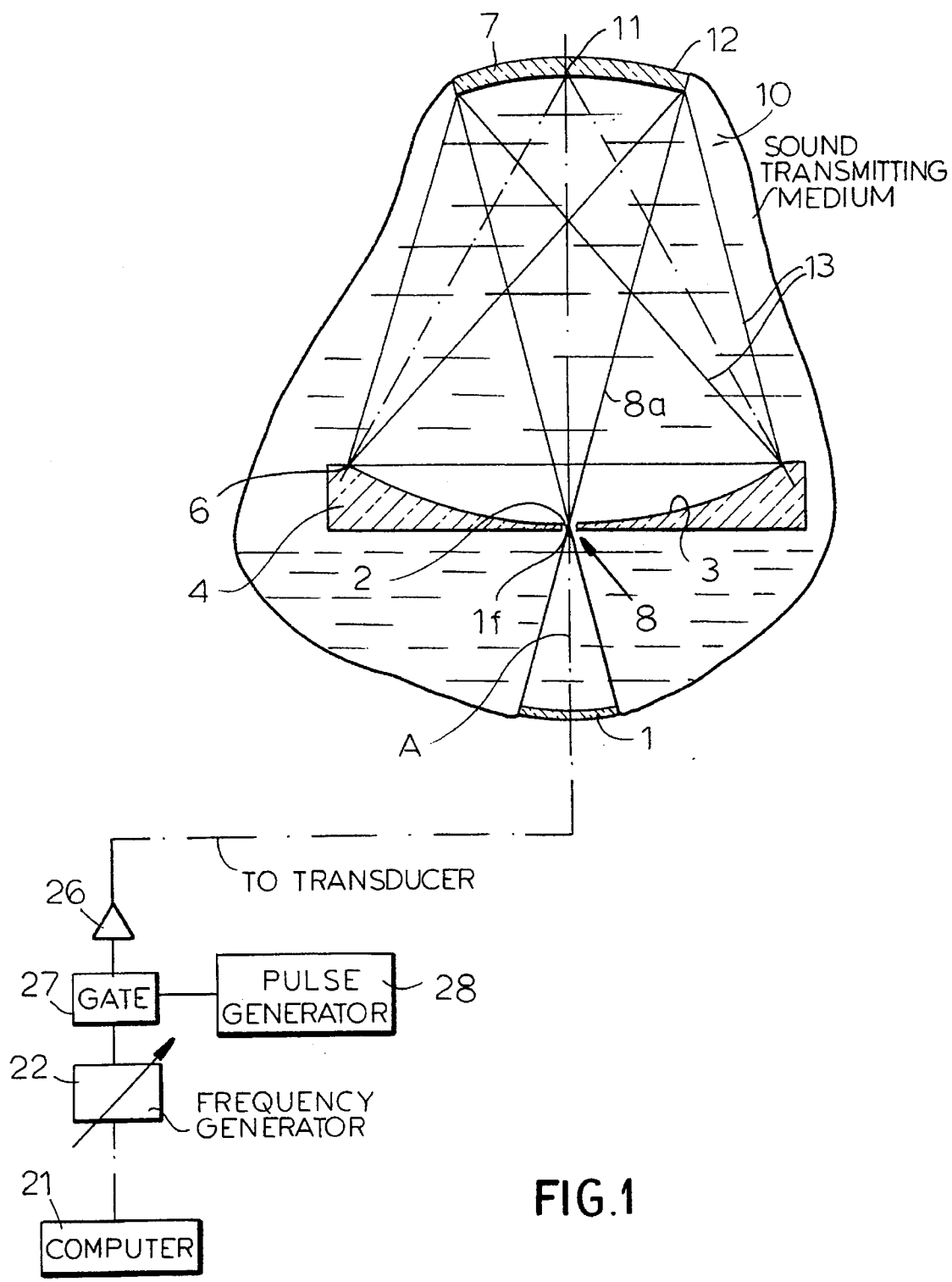
FIG. 1 is a schematic axial section through an apparatus embodying the invention.

FIG. 1 shows the construction of the apparatus in accordance with the principles of the invention. A focusing transducer 1, whose focal point If is located in a hole 2 of a carrier 4, is provided along an axis A of the apparatus below the carrier 4, the hole 2 of which is a point source for ultrasonic waves which are radiated in a cone 8a toward a support 7, the entire area of which is irradiated by these waves.

Figure 4:
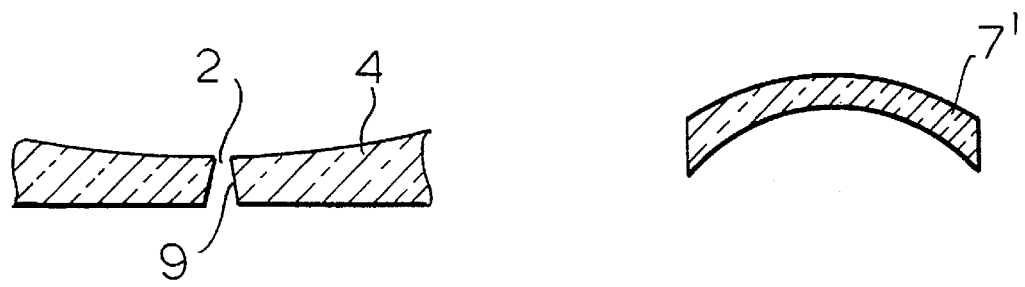
FIG. 4 is a cross sectional view through the carrier showing the configuration of the hole.

The hole 2 can have a conical configuration as shown at 9 in FIG. 4 and can converge in the direction of the axis A toward the support 7.

A body of liquid 10 forms a sound-transmitting medium between the point source 8 and the support 7 (see U.S. Pat. No. 5,258,222).

The support 4 has a spherical surface 3 which has a center point 11 in the middle of the support surface 12 of the support 7 which is transmissive to ultrasonic waves. In the embodiment shown in FIG. 1, the support 7 is a convex-concave disk of constant wall thickness, the convex side of which serves as a resting surface for the object, namely, the tip of a finger when the apparatus is used to determine the contours of the finger, i.e. the fingerprint.

Figure 2:
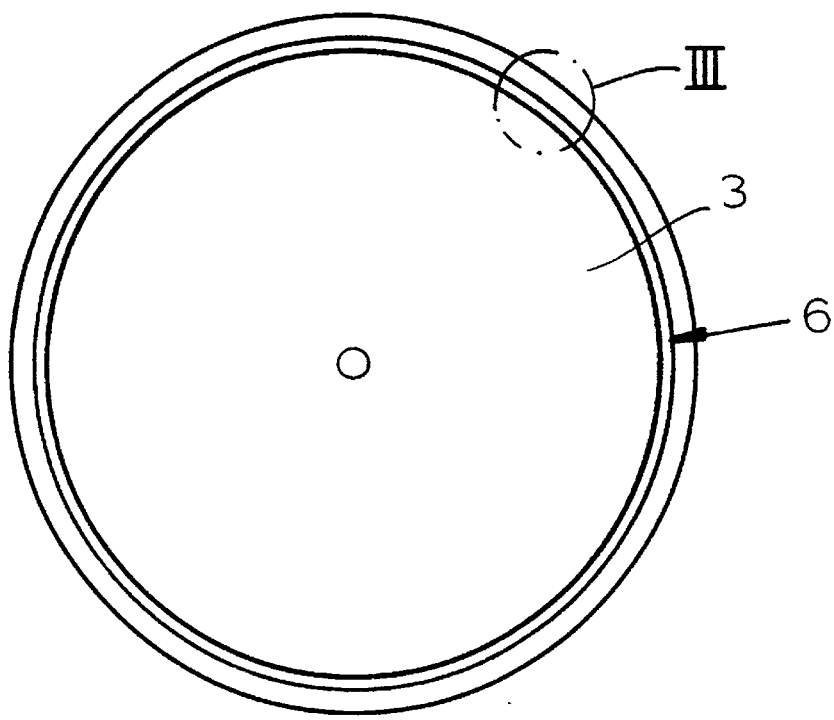
FIG. 2 is a plan view of the carrier surface provided with the receiving transducer ring.
Figure 3:
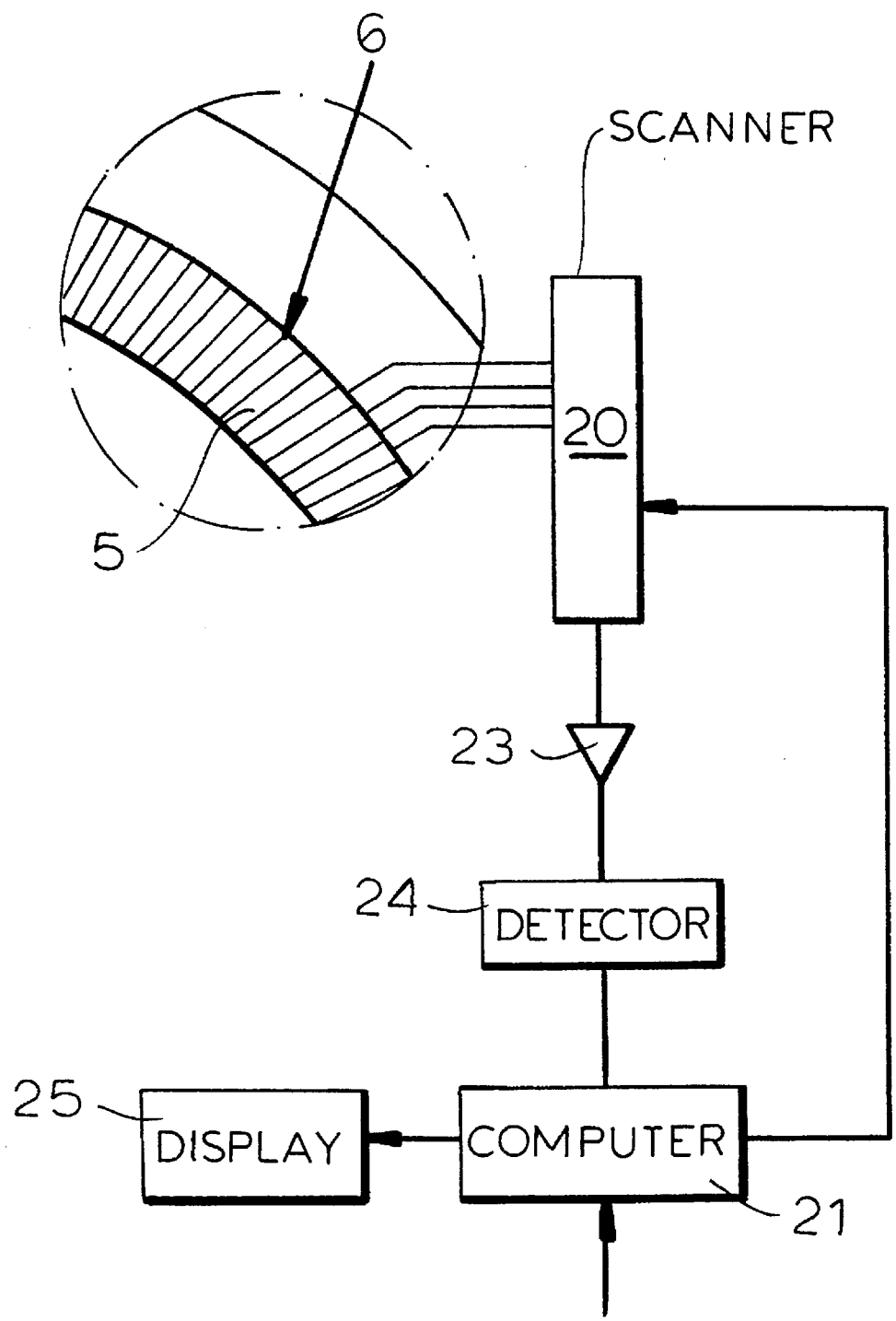
FIG. 3 is a detail view of he region III of FIG. 2 drawn to a larger scale.

On the surface 3 of the carrier 4, as best seen from FIGS. 2 and 3, numerous small receiving transducers 5 are provided closely adjacent one another in a receiving transducer ring or annular array 6.

The surface 3, optionally as long as the region in which the sensors 5 are disposed, is spherical.

Figure 5:
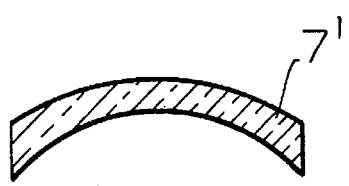
FIG. 5 is a cross sectional view of another support which can be substituted for the constant thickness support of FIG. 1.

Instead of a disk as a support, I can use a convexo-concave or concavo-convex lens as shown at 7' in FIG. 5. In either case, the convex side serves as a resting surface for the object. The support 7, 7' focuses the backscattered ultrasonic waves upon the receiving transducer ring 6. In this manner sufficient energy is transmitted to the receiving transducers. The medium 10 may be water. However, it is also possible to provide a light body as the sound-transmitting medium, especially glass or plastic. The backscattered waves have been shown at 13 in FIG. 1.

The ultrasonic waves focused into the hole 2 from the transducer 1 travel toward the support 7 with a spherical wave front and the backscatter is picked up by the sensors 5. The backscatter patterns represent not only the surface structure of the finger but structures immediately below the surface which contribute to the growth of the epidermis. The total area of the support 7 is thus irradiated and as a consequence of the focusing effect of the support, a significant part of the backscatter is focused upon the receiving transducer ring 6, thereby ensuring a distinct diffraction pattern.

It is not essential that the hole 2 be located in the center of the surface 3 of carrier 4 as long as the orientation is such that the backscattered waves from the object fall on the annular receiving transducer ring.

As will be apparent from FIG. 3, the individual transducers 5 can be scanned in succession by the scanner 20 under the control of the computer 21 which can also receive an input from the frequency generator 22 (FIG. 1) so that in each change in frequency the receiving transducers 5 are scanned in sequence. The scanned output is amplified at 23 to feed to a detector 24, the DC signal which is supplied to the computer 21 which provides a display at 25 of the duplication pattern or some other indicia resulting from evaluation of the fingerprint.

The frequency generator 22 can supply an amplifier 26 feeding the transducer 1 through a gate 27 triggered by pulses from a pulse generator or pulse source 28 to allow bursts of pulses from the frequency generator to be supplied to the emitting transducer 1. The frequency generator 22 can be variable within the ultrasonic range to allow, for example, the aforementioned 20 frequencies to be selected.

I claim:

1. An ultrasonic apparatus for determining surface and surface-adjacent structures, comprising:

a support composed of a material which is transmissive to incident, reflected and backscattered ultrasonic waves, said support being formed with a resting surface upon which a surface to be determined of an object can rest;

receiving means comprising a body spaced from said support at a side thereof opposite said resting surface, said body having a spherically concave surface turned toward said support, said spherically concave surface having a center of curvature at a middle of said resting surface, said spherically concave surface being provided with a throughgoing hole passing through said body having a diameter ranging from an order of magnitude of a wavelength of said ultrasonic waves up to ten times said wavelength, said hole being located along an axis of said spherically concave surface through said center of curvature, said receiving means including transducer means responsive to ultrasonic backscattered waves from said object for outputting signals characterizing said surface to be determined, said support focussing ultrasonic waves toward said body;

an ultrasonic wave transmitting medium filling a space between said spherically concave surface and said support for transmitting ultrasonic waves emitted from said hole to said support and to said object on said resting surface and for transmitting said backscattered waves from said object to said receiving means and to said transducer means; and a transmitting transducer disposed on an opposite side of said hole from said support for outputting ultrasonic waves and focussing the outputted ultrasonic waves upon said hole as a focal point for said outputted ultrasonic waves, whereby ultrasonic waves are emitted from said hole as a point source of spherical waves into said medium and onto said support for simultaneous irradiation of an entire area of the resting surface with said spherical waves.

2. The ultrasonic apparatus defined in claim 1 wherein said transducer means includes a multiplicity of receiving transducer elements arrayed around said hole.

3. The ultrasonic apparatus defined in claim 1 wherein said support is a convexo-concave lens.

4. The ultrasonic apparatus defined in claim 1 wherein said support is a concavo-convex lens.

5. The ultrasonic apparatus defined in claim 1 wherein said support is a convexo-concave disk of uniform thickness.

6. The ultrasonic apparatus defined in claim 2 wherein said receiving transducer elements are disposed adjacent one another in an array.

7. The ultrasonic apparatus defined in claim 6 wherein said array is a ring.

8. The ultrasonic apparatus defined in claim 6 wherein each of said transducer elements has a reception aperture of a diameter of the same order of magnitude as the wavelength of the ultrasonic waves emitted by said hole into said medium.

9. The ultrasonic apparatus defined in claim 1, further comprising means connected with said transmitting transducer for pulsing said outputted ultrasonic waves.

10. The ultrasonic apparatus defined in claim 1, further comprising means connected with said transmitting transducer for varying a frequency of said outputted ultrasonic waves.

11. The ultrasonic apparatus defined in claim 1 wherein said hole is located at a center of said body.

12. The ultrasonic apparatus defined in claim 1 wherein said hole has a funnel shape converging from a side of said transmitting transducer to a side of said support.

13. The ultrasonic apparatus defined in claim 12 wherein said transducer means includes a multiplicity of receiving transducer elements arrayed around said hole, said hole being located at a center of said body.

14. The ultrasonic apparatus defined in claim 13 wherein said support is a convexo-concave lens.

15. The ultrasonic apparatus defined in claim 13 wherein said support is a convexo-concave disk of uniform thickness.

16. The ultrasonic apparatus defined in claim 13 wherein said receiving transducer elements are disposed adjacent one another in an array.

17. The ultrasonic apparatus defined in claim 16 wherein said array is a ring.

18. The ultrasonic apparatus defined in claim 17 wherein each of said transducer elements has a reception aperture of a diameter of the same order of magnitude as the wavelength of the ultrasonic waves emitted by said hole into said medium.

19. The ultrasonic apparatus defined in claim 18, further comprising means connected with said transmitting transducer for pulsing said outputted ultrasonic waves.

20. The ultrasonic apparatus defined in claim 19, further comprising means connected with said transmitting transducer for varying a frequency of said outputted ultrasonic waves.

* * * * *